US008119430B2

(12) United States Patent
Park et al.

(10) Patent No.: US 8,119,430 B2
(45) Date of Patent: Feb. 21, 2012

(54) METHOD OF MANUFACTURING SEMICONDUCTOR NANOWIRE SENSOR DEVICE AND SEMICONDUCTOR NANOWIRE SENSOR DEVICE MANUFACTURED ACCORDING TO THE METHOD

(75) Inventors: Chan-Woo Park, Daejeon (KR); Chang-Geun Ahn, Daejeon (KR); Jong-Heon Yang, Daejeon (KR); In-Bok Baek, Cheongju-si (KR); Chil-Seong Ah, Daejeon (KR); An-Soon Kim, Daejeon (KR); Tae-Youb Kim, Seoul (KR); Gun-Yong Sung, Daejeon (KR); Seon-Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 215 days.

(21) Appl. No.: 12/494,846

(22) Filed: Jun. 30, 2009

(65) Prior Publication Data

US 2010/0090197 A1 Apr. 15, 2010

(30) Foreign Application Priority Data

Oct. 10, 2008 (KR) .................. 10-2008-0099614

(51) Int. Cl.
*H01L 21/00* (2006.01)
(52) U.S. Cl. ............... 438/49; 257/414; 257/E29.07; 977/959
(58) Field of Classification Search .......... 257/39, 257/253, 347, 414, E29.07, E21.404; 438/49; 977/887–889, 920, 924, 925, 944–946, 957–959
See application file for complete search history.

(56) References Cited

U.S. PATENT DOCUMENTS

| 5,679,475 | A | * | 10/1997 | Yamagata et al. | ............ 428/698 |
| 6,855,606 | B2 | * | 2/2005 | Chen et al. | .................... 438/283 |
| 6,870,235 | B2 | | 3/2005 | Abstreiter et al. | |
| 7,087,506 | B2 | * | 8/2006 | Anderson et al. | ............ 438/488 |
| 7,294,526 | B2 | | 11/2007 | Li et al. | |
| 2004/0136866 | A1 | * | 7/2004 | Pontis et al. | .................... 422/57 |
| 2005/0121706 | A1 | * | 6/2005 | Chen et al. | .................... 257/288 |
| 2005/0189651 | A1 | * | 9/2005 | Hirose et al. | .................. 257/745 |

(Continued)

FOREIGN PATENT DOCUMENTS

KR 1020080025489 3/2008

(Continued)

OTHER PUBLICATIONS

Cui, Yi et al., "Nanowire Nanosensors for Highly Sensitive and Selective Detection of Biological and Chemical Species," *Science*, vol. 293:1289-1292 (2001).

(Continued)

*Primary Examiner* — William F Kraig
(74) *Attorney, Agent, or Firm* — Nelson Mullins Riley & Scarborough LLP; EuiHoon Lee, Esq.

(57) ABSTRACT

Provided are a method of manufacturing a semiconductor nanowire sensor device and a semiconductor nanowire sensor device manufactured according to the method. The method includes preparing a first conductive type single crystal semiconductor substrate, forming a line-shaped first conductive type single crystal pattern from the first conductive type single crystal semiconductor substrate, forming second conductive type epitaxial patterns on both sidewalls of the first conductive type single crystal pattern, and forming source and drain electrodes at both ends of the second conductive type epitaxial patterns.

9 Claims, 6 Drawing Sheets

U.S. PATENT DOCUMENTS

| | | |
|---|---|---|
| 2006/0054936 A1 | 3/2006 | Lieber et al. |
| 2008/0157130 A1* | 7/2008 | Chang .......................... 257/288 |
| 2009/0250689 A1* | 10/2009 | Colli .............................. 257/39 |
| 2010/0270530 A1* | 10/2010 | Park et al. ........................ 257/9 |

FOREIGN PATENT DOCUMENTS

| | | |
|---|---|---|
| KR | 1020080050958 | 6/2008 |
| KR | 10-2009-0058883 | 6/2009 |
| KR | 2009058883 A * | 6/2009 |
| WO | WO 2008035273 A2 * | 3/2008 |
| WO | WO-2008/069477 A1 | 6/2008 |
| WO | WO 2009072722 A1 * | 6/2009 |

OTHER PUBLICATIONS

Kim, Ansoon et al., "Ultrasensitive, label-free, and real-time immunodetection using silicon field-effect transistors," *Applied Physics Letters*, vol. 91:103901-1-103901-3 (2007), Sep. 4, 2007.

Stern, Eric et al., "Label-free immunodetection with CMOS-compatible semiconducting nanowires," *Nature*, vol. 445:519-522 (2007), Feb. 1, 2007.

* cited by examiner

METHOD OF MANUFACTURING SEMICONDUCTOR NANOWIRE SENSOR DEVICE AND SEMICONDUCTOR NANOWIRE SENSOR DEVICE MANUFACTURED ACCORDING TO THE METHOD

CROSS-REFERENCE TO RELATED APPLICATIONS

This U.S. non-provisional patent application claims priority under 35 U.S.C. §119 of Korean Patent Application No. 10-2008-0099614, filed on Oct. 10, 2008, the entire contents of which are hereby incorporated by reference.

BACKGROUND OF THE INVENTION

The present invention disclosed herein relates to a method of manufacturing a semiconductor nanowire sensor device and a semiconductor nanowire sensor device manufactured according to the method, and more particularly, to a method of manufacturing a semiconductor nanowire sensor device using an epitaxial growth process and a patterning process, and a semiconductor nanowire sensor device manufactured according to the method.

According as a high integration of a semiconductor device progresses, active research is being carried out on nanomaterial to address limitations in scaling down silicon-based semiconductor devices and study new physical phenomena. The nanomaterial includes nanowires, nanobelts, nanoribbons, and nanorods. Specifically, research on the nanowires is being widely carried out. The nanowires can be applied to next-generation electronic devices, bio-sensors, optoelectronic devices, and energy devices.

To apply the nanowires to various fields, it is necessary to make the sizes and lengths of the nanowires uniform, and uniformly arrange the nanowires.

The nanowires are formed using a bottom-up method such as a vapor-liquid-solid (VLS) growth method. According to the VLS growth method, the diameters and densities of the nanowires are adjusted by controlling metal catalyst nanoparticles. However, in the case of the bottom-up method, it is difficult to make the diameters of the nanoparticles uniform and arrange the nanoparticles at a desired position.

To solve these limitations, a technology is suggested in which a nanowire is formed on a silicon-on-insulator (SOI) substrate through top-down type semiconductor micro-machining processes such as a lithography process and an etch process, and then the nanowire is used as a channel to detect biomaterial. However, it is necessary that the nanowire used as the channel has a line width ranging from several nm to tens of nm to detect highly sensitive biomaterial, and a high-cost and low-efficiency nanopatterning technology such as an electron beam lithography technology is required to realize the line width ranging from several nm to tens of nm through the top-down semiconductor micro-machining process. In addition, since a process of manufacturing the SOI substrate used in nano-bio sensors is more complicated and more expensive than a process of manufacturing a typical bulk silicon substrate, it is difficult to secure economic efficiency in the mass production of the nano-bio sensors.

SUMMARY OF THE INVENTION

The present invention provides a method of manufacturing a semiconductor nanowire sensor device, which is adapted for forming a nanowire on a bulk semiconductor substrate.

The present invention also provides a semiconductor nanowire sensor device including a nanowire on a bulk semiconductor substrate.

The object of the present invention is not limited to the aforesaid, but other objects not described herein will be clearly understood by those skilled in the art from descriptions below.

Embodiments of the present invention provide methods of manufacturing a semiconductor nanowire sensor device, the methods including: preparing a first conductive type single crystal semiconductor substrate; forming a line-shaped first conductive type single crystal pattern from the first conductive type single crystal semiconductor substrate; forming second conductive type epitaxial patterns on both sidewalls of the first conductive type single crystal pattern; and forming source and drain electrodes at both ends of the second conductive type epitaxial patterns.

In other embodiments of the present invention, semiconductor nanowire sensor devices include: a first conductive type single crystal semiconductor substrate; a line-shaped first conductive type single crystal semiconductor pattern disposed on the first conductive type single crystal semiconductor substrate; second conductive type epitaxial patterns disposed on both sidewalls of the first conductive type single crystal semiconductor pattern; and source and drain electrodes disposed at both ends of the second conductive type epitaxial patterns.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF PREFERRED EMBODIMENTS

Figure 1:
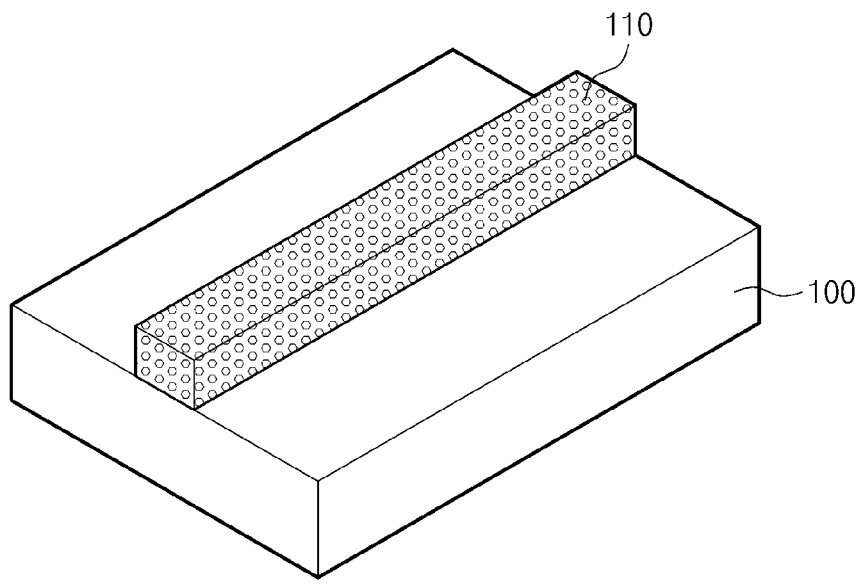
FIGS. 1 through 7 are schematic views illustrating a method of manufacturing a semiconductor nanowire sensor device according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explain a specific exemplary embodiment while not limiting the present invention. The terms of a singular form may include plural forms unless referred to the contrary. The meaning of "include," "comprise," "including," and/or "comprising," specifies a property, a region, a fixed number, a step, a process, an element and/or a component but does not exclude other properties, regions, fixed numbers, steps, processes, elements and/or components. It will be understood that when an element such as a layer, film, region, or substrate is referred to as being "on" another element, it can be directly on the other element or intervening elements may also be present.

Additionally, the embodiment in the detailed description will be described with cross-sectional views and/or plan views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a semiconductor package region. Thus, this should not be construed as limited to the scope of the present invention.

Hereinafter, it will be described about exemplary embodiments of the present invention in conjunction with the accompanying drawings.

FIGS. 1 through 7 are schematic views illustrating a method of manufacturing a semiconductor nanowire sensor device according to an embodiment of the present invention.

Referring to FIG. 1, a first conductive type single crystal semiconductor substrate 100, to be provided with nanowires, is prepared. A bulk silicon substrate, a bulk germanium substrate, or a bulk silicon-germanium substrate may be used for the single crystal semiconductor substrate 100.

A line-shaped mask pattern 110 is formed on the first conductive type single crystal semiconductor substrate 100. The mask pattern 110 may have a line width ranging from about 1 μm to about 100 μm. The mask pattern 110 has an etch selectivity with respect to the single crystal semiconductor substrate 100. For example, the mask pattern 110 may be formed of photoresist, silicon nitride, or silicon oxide.

Figure 2:
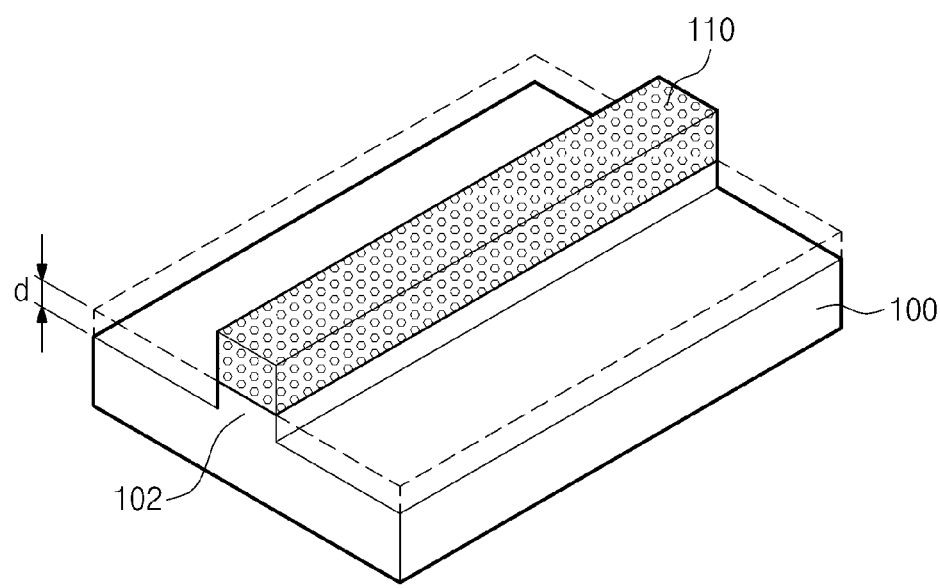

Referring to FIG. 2, the first conductive type single crystal semiconductor substrate 100 is etched using the line-shaped mask pattern 110 as an etch mask. The single crystal semiconductor substrate 100 may be recessed with a depth 'd' ranging from about 1 nm to about 100 nm from its surface. The etching of the semiconductor substrate 100 is adjusted by controlling process conditions such as the type of an etch gas, the flow rate ratio of an etch gas, and an etch time.

Figure 3:
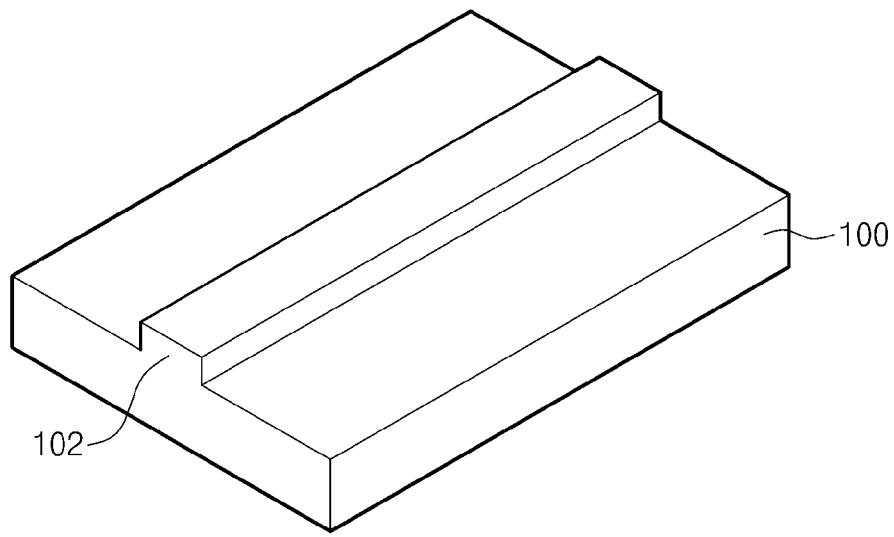

After that, referring to FIG. 3, the mask pattern 110 may be removed to provide a line-shaped first conductive type single crystal pattern 102 protruding from the surface of the single crystal semiconductor substrate 100. That is, the first conductive type single crystal pattern 102 may have a height ranging from about 1 nm to about 100 nm, and a line width ranging from about 1 μm to about 100 μm.

Figure 4:
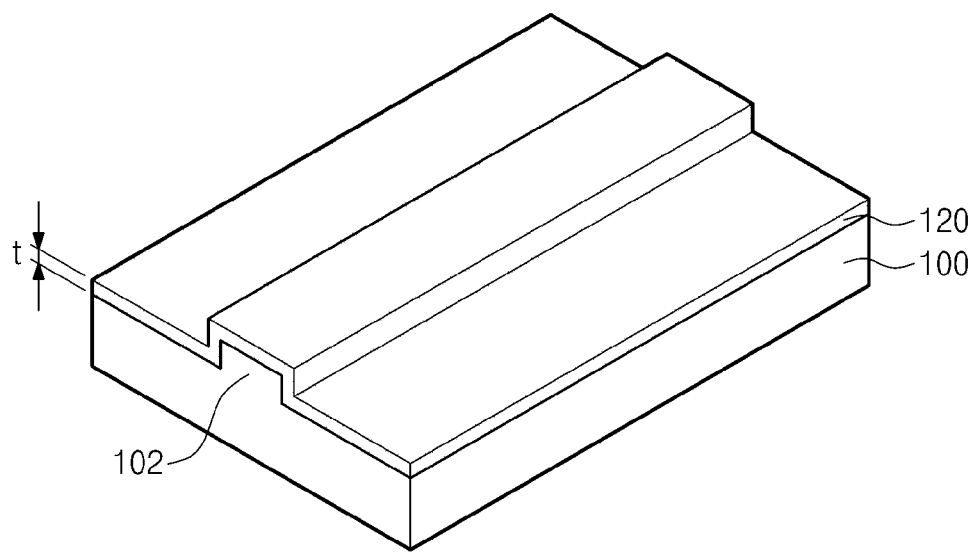

Referring to FIG. 4, a second conductive type epitaxial layer 120 is formed on the entire surfaces of the first conductive type single crystal semiconductor substrate 100 and the first conductive type single crystal pattern 102.

Particularly, an epitaxial growth process is performed on the entire surfaces of the first conductive type single crystal semiconductor substrate 100 and the first conductive type single crystal pattern 102. Since the epitaxial growth process is performed on the entire surfaces without a mask, the epitaxial layer 120 conforms with the entire surfaces of the first conductive type single crystal semiconductor substrate 100 and the first conductive type single crystal pattern 102. Since the epitaxial layer 120 is grown using the single crystal semiconductor substrate 100 and the single crystal pattern 102 as a seed layer, the epitaxial layer 120 may have a single crystal structure. The epitaxial layer 120 may be grown to a thickness 't' ranging from about 1 nm to about 100 nm. The line width of the nanowire may depend on the thickness of the epitaxial layer 120.

While growing the epitaxial layer 120, the epitaxial layer 120 may be doped in-situ with a dopant such as boron, phosphorous, arsenic, indium, or antimony, or an ion implantation process may be performed. Accordingly, the epitaxial layer 120 may have the second conductive type that is opposite to the first conductive type. That is, when the first conductive type is a p-type conductive type, the epitaxial layer 120 may be doped with an n-type dopant to have the second conductive type.

Figure 5:
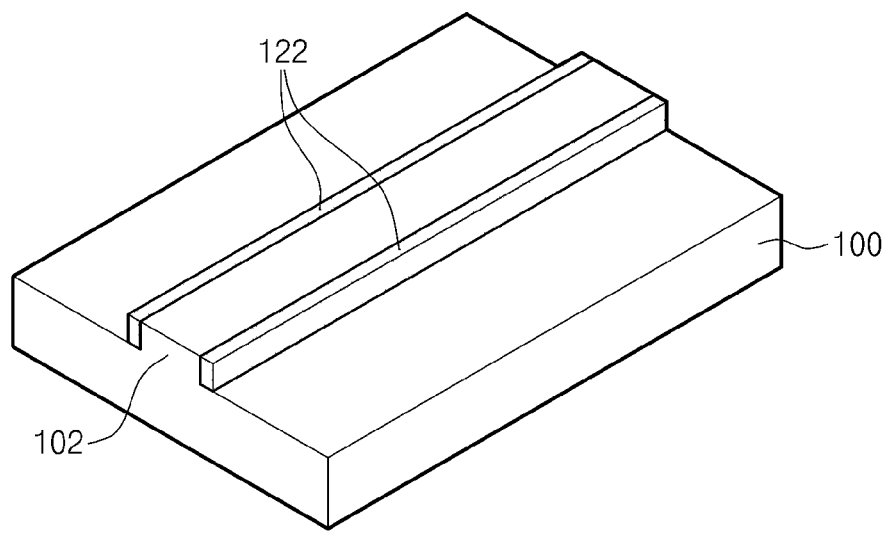

Referring to FIG. 5, second conductive type epitaxial patterns 122 are formed on both sidewalls of the line-shaped first conductive type single crystal pattern 102 protruding from the first conductive type single crystal semiconductor substrate 100. The second conductive type epitaxial patterns 122 may be formed by performing a blanket anisotropic etch process on the second conductive type epitaxial layer 120. The second conductive type epitaxial patterns 122 may have a line width ranging from about 1 nm to about 100 nm. That is, as the nanowires of the nanowire sensor device, the line-shaped second conductive type epitaxial patterns 122 may be formed, having a line width ranging from several nm to several tens of nm. The second conductive type epitaxial patterns 122 may be used as channel regions in the nanowire sensor device according to the current embodiment of the present invention.

Since the second conductive type epitaxial patterns 122 are formed by performing the blanket anisotropic etch process on the epitaxial layer 120, the second conductive type epitaxial patterns 122 may be formed in pair on the both sidewalls of the first conductive type single crystal pattern 102. In other words, the nanowires according to the current embodiment of the present invention may be provided in pair with the first conductive type single crystal pattern 102 there-between, and have the second conductive type that is opposite to the first conductive type.

As such, since the first conductive type single crystal pattern 102 is opposite in conductive type to the second conductive type epitaxial patterns 122, when a reverse bias is applied between the second conductive type epitaxial pattern 122 and both the first conductive type single crystal semiconductor substrate 100 and the first conductive type single crystal pattern 102, the second conductive type epitaxial pattern 122 may be electrically isolated through a junction isolation from both the first conductive type single crystal semiconductor substrate 100 and the first conductive type single crystal pattern 102.

Figure 6:
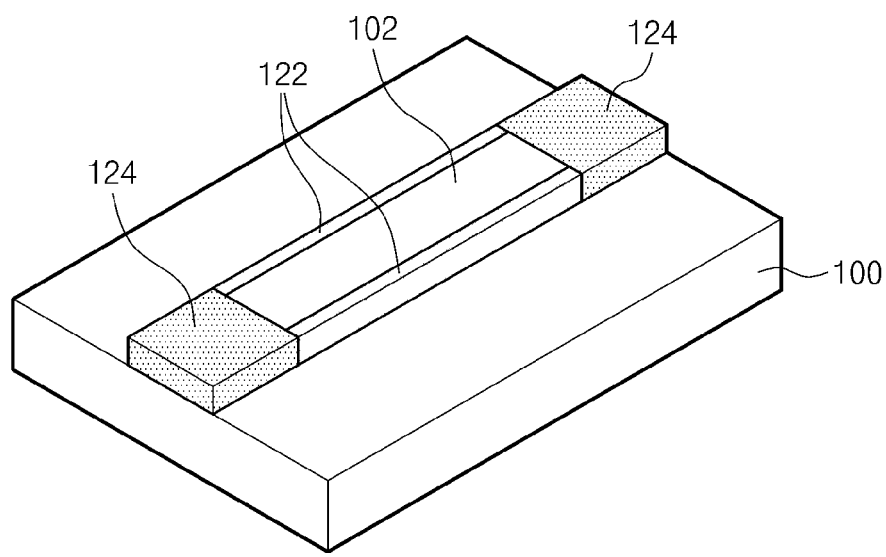

Referring to FIG. 6, second conductive type impurity regions 124 for forming electrodes are formed at both ends of the second conductive type epitaxial patterns 122, that is, at both ends of the nanowires.

Particularly, a mask pattern (not shown) is formed, which exposes the both ends of the second conductive type epitaxial patterns 122. The mask pattern may expose both ends of the first conductive type single crystal pattern 102. That is, the mask pattern may cross and cover the centers of the second conductive type epitaxial patterns 122 and the first conductive type single crystal pattern 102.

The both ends of the second conductive type epitaxial patterns 122 are doped with impurities through the mask pattern covering the centers of the second conductive type epitaxial patterns 122 and the first conductive type single crystal pattern 102. The second conductive type impurity regions 124 may be formed by ion-implanting second conductive type impurities through an ion implantation process. After the second conductive type impurity regions 124 are formed, a heat treating process is performed to remove defects due to the ion implantation process and activate the ion-implanted impurities.

That is, the second conductive type impurity regions 124 may be formed at the both ends of the second conductive type epitaxial patterns 122 and the first conductive type single crystal pattern 102. Accordingly, the second conductive type impurity regions 124 may be connected in common to the second conductive type epitaxial patterns 122.

Figure 7:
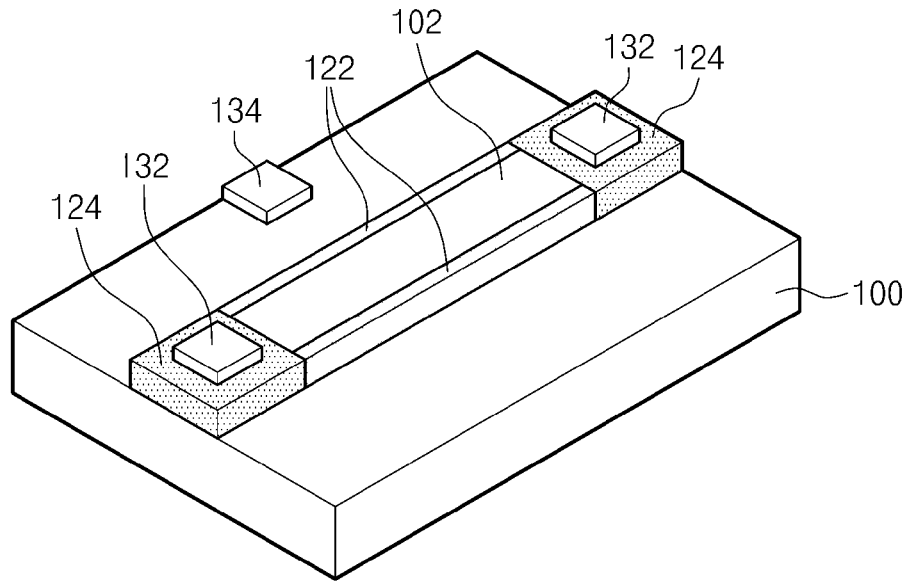

Referring to FIG. 7, ohmic electrodes 132 are formed on the second conductive type impurity regions 124, respectively. An ohmic electrode 134 may be formed on the first conductive type single crystal semiconductor substrate 100. Although not shown, the ohmic electrode 134 may be formed on the first conductive type single crystal pattern 102.

The ohmic electrodes 132 and 134 may be formed of a material exhibiting an ohmic contact characteristic with the second conductive type impurity regions 124 and the single crystal semiconductor substrate 100. For example, the ohmic electrodes 132 and 134 may be formed from a doped polysilicon layer, a metal layer, a conductive metal oxide layer, or a metal silicide layer.

A voltage difference is applied to the ohmic electrodes 132 on the second conductive type impurity regions 124 at the ends of the second conductive type epitaxial patterns 122 such that a current flows through the second conductive type epitaxial patterns 122. A voltage is applied to the ohmic electrode 134 on the first conductive type single crystal semiconductor substrate 100 and/or the first conductive type single crystal pattern 102 such that a reverse bias is applied between the second conductive type epitaxial pattern 122 and both the first conductive type single crystal semiconductor substrate 100 and the first conductive type single crystal pattern 102.

Figure 8:
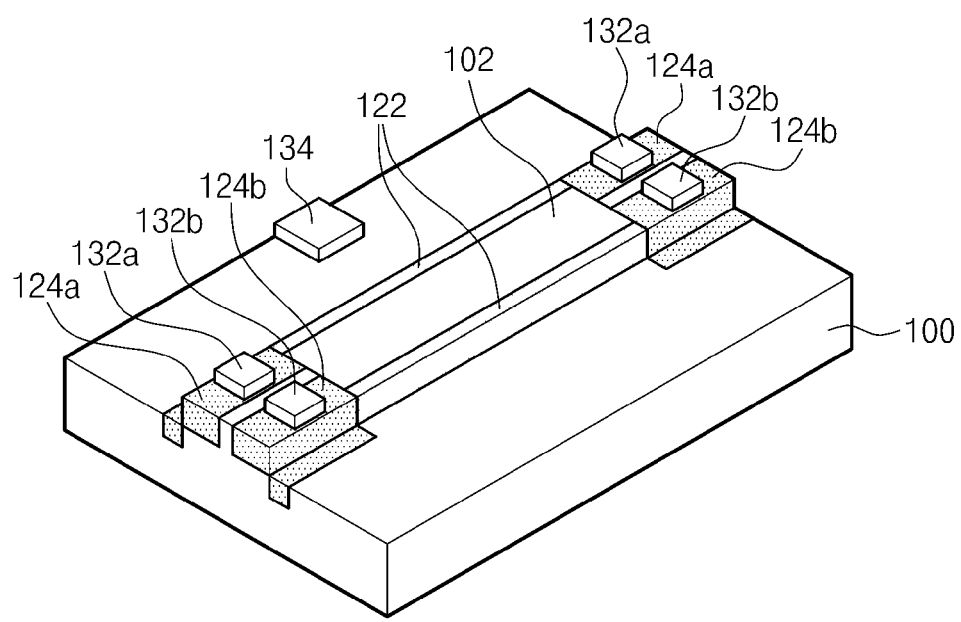
FIG. 8 is a schematic view illustrating a semiconductor nanowire sensor device according to an embodiment of the present invention.

FIG. 8 is a schematic view illustrating a semiconductor nanowire sensor device according to an embodiment of the present invention.

Referring to FIG. 8, in the semiconductor nanowire sensor device according to the current embodiment of the present invention, source and drain electrodes 132a may be formed at the both ends of one of the second conductive type epitaxial patterns 122, and source and drain electrodes 132b may be formed at the both ends of the other of the second conductive type epitaxial patterns 122.

That is, after the second conductive type epitaxial patterns 122, having a line width ranging from several nm to tens of nm, are formed as illustrated in FIG. 5, second conductive type impurity regions 124a are formed at the both ends of one of the second conductive type epitaxial patterns 122, and second conductive type impurity regions 124b are formed at the both ends of the other of the second conductive type epitaxial patterns 122. The second conductive type impurity regions 124a and 124b may be formed partially in the first conductive type single crystal semiconductor substrate 100 and the first conductive type single crystal pattern 102. Ohmic electrodes 132a may be formed on the second conductive type impurity regions 124a, and ohmic electrodes 132b may be formed on the second conductive type impurity regions 124b.

The semiconductor nanowire sensor devices according to the embodiments of the present invention may be used as a bio-sensor detecting biomolecules, which will now be described with reference to FIGS. 9 through 11. The biomolecules, which are organic molecules exhibiting specific strains, have the same meaning as target molecules or analytes in the present disclosure.

Figure 9:
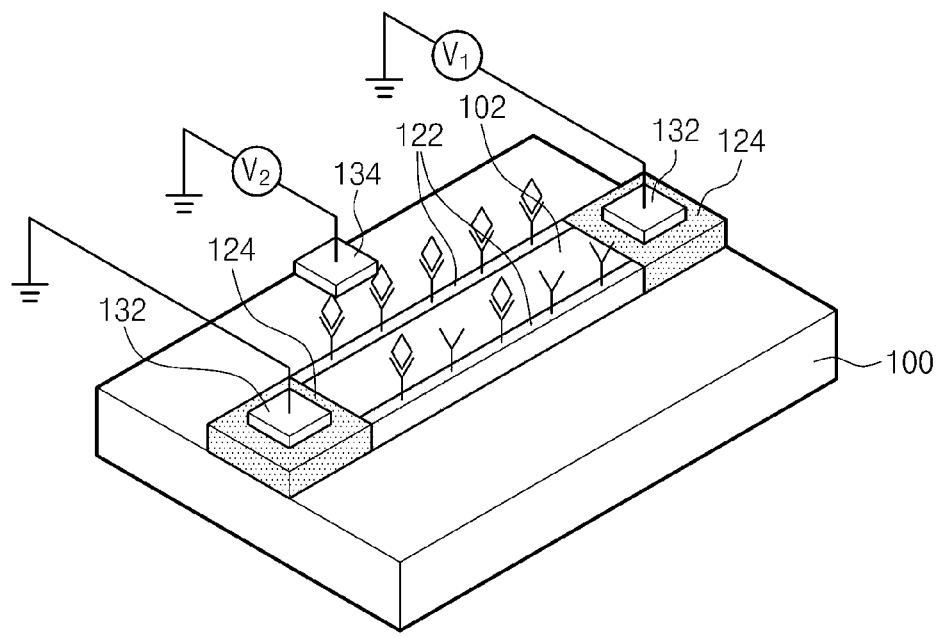
FIGS. 9 and 10 are a perspective view and a cross-sectional view illustrating a biomolecule-detecting device including a semiconductor nanowire sensor device according to an embodiment of the present invention.
Figure 10:
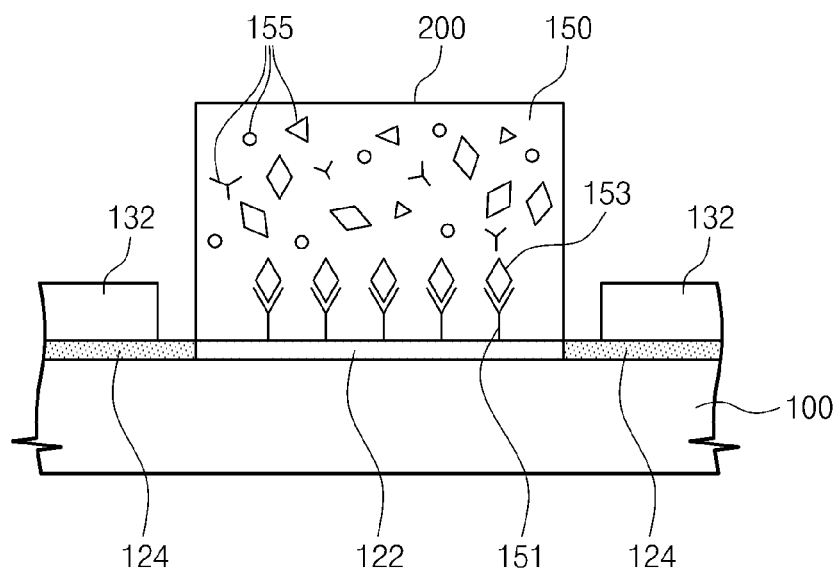

FIGS. 9 and 10 are a perspective view and a cross-sectional view illustrating a biomolecule-detecting device including a semiconductor nanowire sensor device according to an embodiment of the present invention. FIG. 11 is a schematic view illustrating one of probe molecules 151 immobilized to the semiconductor nanowire sensor device according to an embodiment of the present invention.

Referring to FIGS. 9 and 10, in the semiconductor nanowire sensor device, a fluid channel 200 for supplying solutions may be disposed on the second conductive type epitaxial pattern 122 equivalent to a channel region. Particularly, the fluid channel 200 may be disposed on the first conductive type single crystal pattern 102 protruding from the first conductive type single crystal semiconductor substrate 100 and disposed on the second conductive type epitaxial pattern 122.

When appropriate voltages are applied to the ohmic electrodes 132 and 134, the probe molecules 151, binding with target molecules that will be detected, are immobilized to the channel region, that is, to a surface of the second conductive type epitaxial pattern 122 disposed between the second conductive type impurity regions 124.

Particularly, a voltage difference $V_1$ is applied to the ohmic electrodes 132 equivalent to source and drain electrodes, so that a current I flows through the second conductive type epitaxial pattern 122. A voltage $V_2$ is applied to the ohmic electrode 134 disposed on the first conductive type single crystal semiconductor substrate 100 such that a reverse bias is supplied to the first conductive type single crystal semiconductor substrate 100 and the second conductive type epitaxial pattern 122.

The probe molecules 151 may be immobilized directly to the surface of the second conductive type epitaxial pattern 122, or immobilized to the surfaces using organic molecules as media. A method of immobilizing the probe molecules 151 will now be described in detail with reference to FIG. 11.

According to biomolecules (i.e. target molecules 153) to be detected, the probe molecules 151 may be proteins, cells, viruses, or nucleic acids. The proteins may be any biomolecules such as antigens, antibodies, matrix proteins, enzymes, and coenzymes. The nucleic acids may be DNA, RNA, PNA, LNA or a combination thereof.

The probe molecules 151 may be immobilized to a surface of the protruding first conductive type single crystal pattern 102 as well as to the surface of the second conductive type epitaxial pattern 122. However, the reverse bias, supplied to the second conductive type epitaxial pattern 122 and the first conductive type single crystal pattern 102, prevents the probe molecules 151 immobilized to the surface of the first conductive type single crystal pattern 102 from affecting the channel region (i.e., the second conductive type epitaxial pattern 122).

After the probe molecules 151 are immobilized to the second conductive type epitaxial patterns 122, a solution 150 containing the target molecules 153 is provided to the surface of the second conductive type epitaxial pattern 122. The solution 150 may further contain nonspecific molecules 155 that do not bind with the probe molecules 151.

The target molecules 153 (or analytes), coming from a living body, are biomolecules exhibiting a specific strain. For example, the target molecules 153 may be proteins, nucleic acids, organic molecules, inorganic molecules, oxides, or metal oxides. The proteins may be any biomolecules such as antigens, antibodies, matrix proteins, enzymes, and coenzymes. The nucleic acids may be DNA, RNA, PNA, LNA or a combination thereof.

When the solution 150 containing the target molecules 153 is supplied to the second conductive type epitaxial patterns 122, the target molecules 153 bind with the probe molecules 151 on the surfaces of the second conductive type epitaxial patterns 122.

The binding of the probe molecules 151 with the target molecules 153 on the surfaces of the second conductive type epitaxial patterns 122 may be any binding, known to those skilled in the art, including nucleic acid hybridization, antigen-antibody reaction, and enzyme link reaction.

After the target molecules 153 bind with the probe molecules 151, the target molecules 153 provide new positive charge or new negative charge to the surface of the second conductive type epitaxial pattern 122. Accordingly, the amount of the current I flowing through the second conductive type epitaxial pattern 122 may depend on the amount of net charge (positive charge or negative charge) of the target molecules 153.

Thus, the amount of the current I flowing through the second conductive type epitaxial pattern 122 are measured according to the target molecules 153 binding the probe molecules 151, so as to detect the presence and the amount of the target molecules 153.

Figure 11:
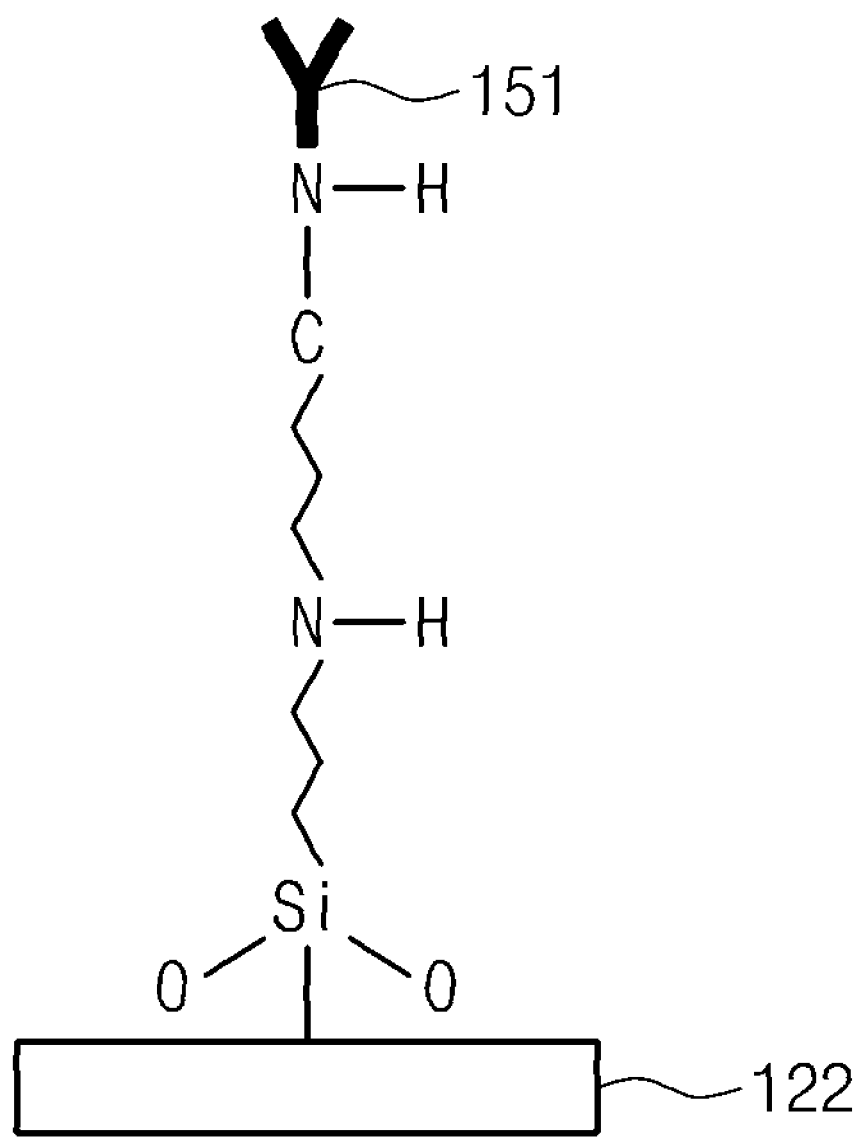
FIG. 11 is a schematic view illustrating a probe molecule immobilized to a semiconductor nanowire sensor device according to an embodiment of the present invention.

Referring to FIG. 11, the method of immobilizing the probe molecule 151 to the surface of the second conductive type epitaxial pattern 122 will now be described in detail. A method of immobilizing a monoclonal antibody of prostate specific antigen (anti-PSA) will be exemplified. The monoclonal anti-PSA is a probe molecule adapted for detecting PSA that is a target molecule.

To immobilize the probe molecule 151, a surface-treating process may be performed on the surface of the second conductive type epitaxial pattern 122 equivalent to the channel region between the ohmic electrodes 132 that are source and drain electrodes. For example, a carboxyl group (—COOH), a thiol group (—SH), a hydroxyl group (—OH), a silane group, an amine group, or an epoxy group may be induced on the surface of the second conductive type epitaxial pattern 122 after the surface-treating process.

For example, an $O_2$ plasma ashing process is performed on the surface of the second conductive type epitaxial pattern 122 to form the hydroxyl group (—OH).

An ethanol solution, in which an 1% aminopropyltriethoxy silane (APTES) is dispersed, is supplied to the surface of the second conductive type epitaxial pattern 122 provided with the hydroxyl group (—OH), then an agitating process is performed for a predetermined time, and then washing and drying processes are performed.

Then, a 25 weight percent (wt %) glutaraldehyde solution is supplied to the surface of the second conductive type epitaxial pattern 122 to form an aldehyde group (—CHO).

After that, a solution containing the probe molecules 151 (e.g., anti-PSA) is supplied to the surface of the second conductive type epitaxial pattern 122 to bind the anti-PSA with the aldehyde group (—CHO). Accordingly, the probe molecule 151 may be immobilized on the surface of the second conductive type epitaxial pattern 122.

According to the present invention, the method of manufacturing a semiconductor nanowire sensor device and the semiconductor nanowire sensor device manufactured according to the method are adapted for forming nanowires having a line width ranging from several nm to tens of nm, on the bulk semiconductor substrate through the lithography process and the epitaxial growth process.

In addition, the nanowire equivalent to the channel region is electrically isolated from the semiconductor substrate through the PN junction, thereby realizing the semiconductor nanowire sensor device on the bulk semiconductor substrate.

Therefore, the reproducibility and reliability of the semiconductor nanowire sensor device are secured, and mass production is achieved at low costs.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method of manufacturing a semiconductor nanowire sensor device, the method comprising:

preparing a first conductive type single crystal semiconductor substrate;

forming a line-shaped first conductive type single crystal pattern from the first conductive type single crystal semiconductor substrate;

forming second conductive type epitaxial patterns on both sidewalls of the first conductive type single crystal pattern; and forming source and drain electrodes at both ends of the second conductive type epitaxial patterns, wherein the forming of the second conductive type epitaxial patterns comprises:

forming a second conductive type epitaxial layer using an epitaxial growth process, on an entire surface of the first conductive type single crystal semiconductor substrate and an entire surface of the first conductive type single crystal pattern; and performing a blanket anisotropic etch process on the second conductive type epitaxial layer to form the second conductive type epitaxial patterns on the both sidewalls of the first conductive type single crystal pattern.

2. The method of claim 1, wherein the first conductive type single crystal pattern has a height ranging from about 1 nm to about 100 nm.

3. The method of claim 1, wherein the forming of the first conductive type single crystal pattern comprises:

forming a line-shaped mask pattern on the first conductive type single crystal semiconductor substrate; and recessing the first conductive type single crystal semiconductor substrate using the mask pattern.

4. The method of claim 3, wherein the mask pattern has a line width ranging from about 1 μm to about 100 μm.

5. The method of claim 1, wherein the second conductive type epitaxial layer is grown to a thickness ranging from about 1 nm to about 100 nm.

6. The method of claim 1, wherein the forming of the source and drain electrodes comprises:

performing a doping process with second conductive type impurities to form second conductive type impurity regions at the both ends of the second conductive type epitaxial patterns; and forming ohmic electrodes on the second conductive type impurity regions, respectively.

7. The method of claim 6, further comprising forming an ohmic electrode on the first conductive type single crystal semiconductor substrate.

8. The method of claim 1, further comprising immobilizing probe molecules binding to target molecules, to surfaces of the second conductive type epitaxial patterns.

9. The method of claim 8, wherein the probe molecule comprises one selected from the group consisting of a nucleic acid, a cell, a virus, a protein, an organic molecule, and an inorganic molecule.

* * * * *